United States Patent
Charles

(10) Patent No.: US 10,172,686 B2
(45) Date of Patent: Jan. 8, 2019

(54) DEVICES AND SYSTEMS FOR STABILIZATION OF SURGEON'S ARM DURING SURGERY

(71) Applicant: Novartis AG, Basel (CH)

(72) Inventor: Steven T. Charles, Memphis, TN (US)

(73) Assignee: Novartis AG, Basel (CH)

( * ) Notice: Subject to any disclaimer, the term of this patent is extended or adjusted under 35 U.S.C. 154(b) by 40 days.

(21) Appl. No.: 15/377,475

(22) Filed: Dec. 13, 2016

(65) Prior Publication Data

US 2017/0172698 A1    Jun. 22, 2017

Related U.S. Application Data

(60) Provisional application No. 62/268,038, filed on Dec. 16, 2015.

(51) Int. Cl.
*A61B 90/60* (2016.01)
*A47B 21/03* (2006.01)

(52) U.S. Cl.
CPC .......... *A61B 90/60* (2016.02); *A47B 21/0371* (2013.01)

(58) Field of Classification Search
USPC ......... 248/118, 118.1, 118.3, 118.5; 128/898
See application file for complete search history.

(56) References Cited

U.S. PATENT DOCUMENTS

| | | | | |
|---|---|---|---|---|
| 1,266,367 A * | 5/1918 | Wilson | ................... | A01K 87/08 248/118 |
| 2,119,325 A * | 5/1938 | Goodhart | ................ | A61M 5/52 248/118 |
| 2,614,558 A * | 10/1952 | Lovell | ....................... | A61F 5/04 248/118 |
| 3,397,688 A | 8/1968 | Gottfried | | |
| 4,913,393 A * | 4/1990 | Wood | ....................... | A61G 5/10 224/407 |
| 5,074,501 A * | 12/1991 | Holtta | ................ | A47B 21/0371 248/118.3 |
| 5,370,346 A * | 12/1994 | Long | .................. | A47B 21/0371 248/118.5 |
| 5,400,787 A | 3/1995 | Marandos | | |
| 5,405,109 A * | 4/1995 | Nordnes | ............ | A47B 21/0371 248/118.3 |
| 5,961,456 A | 10/1999 | Gildenberg | | |
| 6,076,785 A * | 6/2000 | Oddsen, Jr. | ......... | A47B 21/0314 248/118.3 |
| 6,368,332 B1 * | 4/2002 | Salcudean | .............. | A61B 90/50 128/897 |

(Continued)

FOREIGN PATENT DOCUMENTS

GB    2430175 A * 3/2007  .......... A61H 3/0277
WO    2000013571 A1   3/2000

*Primary Examiner* — Alfred J Wujciak

(57) ABSTRACT

Described herein is an arm stabilization member for dampening inadvertent movement of the arm of a user during a surgical procedure, comprising an arm support and a movement mechanism coupled to the arm support. The arm support comprises an outer frame sized to support at least a portion of the user's arm and an inner pad lining an inner surface of the outer frame and configured to conform to the user's arm. The movement mechanism comprises a counterbalance system movably connected by joints and configured to compensate for the gravitational forces exerted by the arm of the user.

16 Claims, 4 Drawing Sheets

(56) References Cited

U.S. PATENT DOCUMENTS

| | | | |
|---|---|---|---|
| 6,464,183 B1 * | 10/2002 | Bouhuijs | A47C 7/54 248/118 |
| 6,656,143 B2 | 12/2003 | Browd | |
| 6,736,360 B1 | 5/2004 | Buczek | |
| 6,786,461 B1 * | 9/2004 | Tsai | A47B 21/0371 248/118.3 |
| 6,923,505 B2 * | 8/2005 | Siminovitch | A47C 7/54 248/118.1 |
| 7,461,423 B2 * | 12/2008 | Rutherford | F16M 11/04 248/118 |
| 7,461,825 B2 | 12/2008 | Olivera et al. | |
| 7,706,858 B1 | 4/2010 | Green et al. | |
| 8,944,064 B2 | 2/2015 | Akram et al. | |
| 9,615,988 B2 * | 4/2017 | Nakamura | A61G 15/10 |
| 2002/0065461 A1 | 5/2002 | Cosman | |
| 2004/0144673 A1 | 7/2004 | Buczek | |
| 2005/0015879 A1 * | 1/2005 | Cuschieri | A61B 90/60 5/623 |
| 2006/0150336 A1 | 7/2006 | Jackson, III | |
| 2007/0284495 A1 | 12/2007 | Charles | |
| 2008/0203249 A1 * | 8/2008 | Priest | A61F 5/3761 248/118 |
| 2010/0249576 A1 | 9/2010 | Askarinya et al. | |
| 2011/0185503 A1 | 8/2011 | Yan | |
| 2012/0138066 A1 | 6/2012 | Akram et al. | |
| 2012/0310079 A1 | 12/2012 | Henning | |
| 2016/0106508 A1 | 4/2016 | Lathrop et al. | |
| 2016/0175178 A1 | 6/2016 | Charles | |

* cited by examiner

DEVICES AND SYSTEMS FOR STABILIZATION OF SURGEON'S ARM DURING SURGERY

FIELD OF THE INVENTION

The present disclosure pertains to devices and methods for stabilization of a user's arm during a surgical procedure. More particularly, but not by way of limitation, the present disclosure pertains to devices and methods for passively and/or actively stabilizing a surgeon's forearm and/or wrist during ocular surgery.

BACKGROUND

Microsurgical procedures in a variety of surgical fields, including, for example, ophthalmology, otolaryngology, and neurosurgery, frequently require precision cutting and/or removing various body tissues. Due to the delicate nature of these procedures, it is important that the hand holding the surgical instrument has a firm support throughout the procedure to facilitate small and precise movements. Even small movements can lead to complication or injury, especially to delicate tissues such as the cornea, lens, and retina. Surgeons may experience problematic involuntary motions during surgery such as tremor due to stress, fatigue, or medical conditions.

Traditional wrist rests used in microsurgery are stationary and firm supports that are secured in a fixed position relative to the operating platform prior to or during the surgery. For example, the Chan wrist rest is the conventional wrist support most commonly used today in microsurgical procedures. The Chan wrist rest is a curved, stationary, horseshoe-shaped bar that is positioned above and behind a patient's head to support the surgeon's arms and wrists during, for example, ophthalmic surgery. The bar of the Chan wrist rest is entirely disposed in a horizontal plane above the patient's head. In the case of eye surgery, this design presents a problem because the surgeon must often adopt uncomfortable and unsuitable wrist and hand positions against the support to accomplish a given surgical maneuver. Moreover, this type of wrist support does not address or attempt to lessen involuntary motions of the surgeon.

There is a need for a support device that permits a surgeon or other operator to comfortably rest his or her hand on the support device while also dampening inadvertent movements of the operator's arm (e.g., involuntary tremors of the forearm and/or wrist). The present invention is directed to addressing these deficiencies in the prior art.

SUMMARY

According to an exemplary aspect, the present disclosure is directed to an arm stabilizing system for dampening inadvertent movement of the arm of a user during a surgical procedure. The system comprises an arm stabilization member arranged to support the arm of the user. In one aspect, the arm stabilization member comprises an arm support and a movement mechanism. In one aspect, the arm support comprises an outer frame sized to support at least a portion of the user's arm and an inner pad lining an inner surface of the outer frame. In one aspect, the inner pad is configured to conform to the user's arm. In one aspect, the movement mechanism is coupled to the arm support, and comprises a counterbalance system having a plurality of links movably connected by joints. In one aspect, the counterbalance system is configured to compensate for the gravitational forces exerted by the arm of the user. In one aspect, the system comprises a brake element configured to arrest movement between two or more of the plurality of links of the counterbalance system.

According to another exemplary aspect, the present disclosure is directed to an arm stabilization member for dampening inadvertent movement of the arm of a user during a surgical procedure, comprising an arm support and a movement mechanism coupled to the arm support. In one aspect, the arm support comprises an outer frame sized to support at least a portion of the user's arm and an inner pad lining an inner surface of the outer frame. In one aspect, the inner pad is configured to conform to the user's arm. In one aspect, the inner pad is formed of a viscoelastic material, such as a viscoelastic foam. In one aspect, the movement mechanism comprises a counterbalance system having a plurality of links movably connected by joints. In one aspect, the counterbalance system is configured to compensate for the gravitational forces exerted by the arm of the user.

In one aspect, the arm stabilizing member further comprises a connector configured to removably couple the arm stabilizing member to an operating table.

In one aspect, the arm stabilizing member further comprises an elongate shaft and a base coupled to the elongate shaft, and the elongate shaft is repositionable along a longitudinal axis of the base.

In one aspect, the counterbalance system includes at least one parallelogram-link structure. In one aspect, the counterbalance system includes at least one gas spring.

In one aspect, the counterbalance system is configured to provide near-neutral weight balance to the arm support through its range of operative motion.

In one aspect, the arm stabilizing member further comprises a control system coupled to the movement mechanism, wherein the joints of the movement mechanism are mechanically responsive to command signals from the control system.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
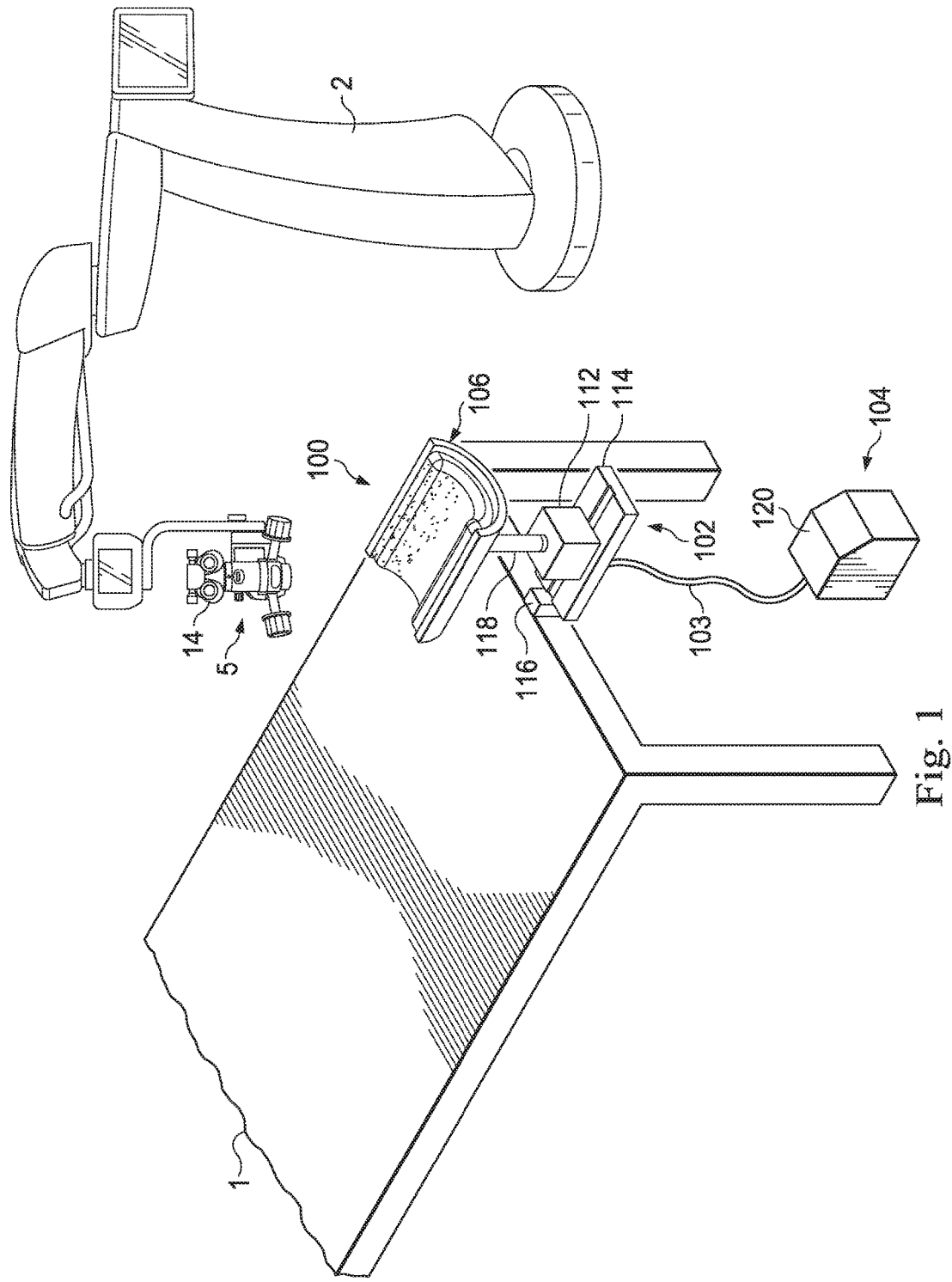
FIG. 1 is an illustration of an exemplary forearm stabilizing system in a surgical environment according to an aspect of the present disclosure implementing the principles and methods described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

In some exemplary aspects, the present disclosure is directed to an arm stabilizing system usable to comfortably support and maintain a user's forearm and/or wrist in a stable position while performing a procedure or process. For example, the arm stabilization system may be particularly useful to a surgeon (or other healthcare professional) performing a surgical procedure, such as, without limitation, an ocular surgical procedure. The arm stabilizing system may maintain the surgeon's (or other healthcare professional's) forearm and/or wrist in a relatively comfortable and stable position within a cradle support in a manner minimizing inadvertent movements, while still allowing for intentional repositioning during the procedure. By minimizing inadvertent movements of the surgeon's arm while permitting intentional movements, the system functions to minimize or counteract potentially dangerous movement such as unintentional tremors (e.g., due to fatigue or medical conditions) while providing a more ergonomic and comfortable experience for surgeons performing ocular surgery. It is to be understood that the embodiments described herein could potentially be used in a variety of procedures requiring fine manual movements, including without limitation, medical procedures, such as otolaryngology surgery, neurosurgery, and others, including manufacturing and craft processes, such as assembly line processes, building small models, and others, and including other implementations where arm support may be helpful to a user.

As described above, conventional arm or wrist rests provide a stationary bar or platform upon which the surgeon may rest a relatively small portion of his or her arm during the surgical procedure. Such conventional wrist supports do little to minimize inadvertent movements of the surgeon, such as tremor and myoclonic jerks. Moreover, such supports may apply continuous pressure to focal areas of the surgeon's forearm or wrist, which may contribute to surgeon discomfort and fatigue. Dampening inadvertent motion by cradling the arm within a curved support while permitting intentional repositioning of the arm stabilizing system throughout the surgical procedure is different than merely providing a stationary support upon which the surgeon may rest his or her arm. In particular, in surgeries using the forearm stabilizing systems described herein, the surgeon's operating forearm and/or wrist is held in a more comfortable and steady position relative to the patient than in surgeries utilizing rigid, fixed wrist support structures. Some embodiments described herein passively dampen inadvertent movements by cushioning the surgeon's forearm within a cradle formed from a high density, viscous material. Some embodiments described herein actively dampen inadvertent movements by utilizing sensor-driven actuators and control systems configured to recognize and reduce unintentional movements of the surgeon's arm. In addition, in some forearm stabilizing systems described herein, the cradle is attached to a movement mechanism that "weightlessly" supports the surgeon's forearm while allowing for free motion in the pitch, yaw, and vertical directions. The reduced motion facilitates better physician control of instruments and tools while minimizing surgeon discomfort and fatigue, thereby possibly contributing to better patient outcomes.

FIG. 1 illustrates a forearm stabilizing system 100 and a surgical arrangement according to an exemplary embodiment. Here, a surgical microscope 5 is attached to a floor stand 2 and suspended above an operating table 1. The forearm stabilizing system 100 includes an arm stabilization member 102, an optional control console 104, an optional communication cable 103, and one or more optional sensors (shown in block diagram form in FIG. 4 as sensors 105) that may be attached directly to the surgeon, the patient, the arm stabilization member 102, or at some other location about the surgical arrangement. In this example implementation, the forearm stabilizing system 100 is attached to and supported by the operating table 1. Here, it is disposed at an end of the operating table 1 and may be particularly situated for a surgeon performing an ocular surgery.

Figure 2:
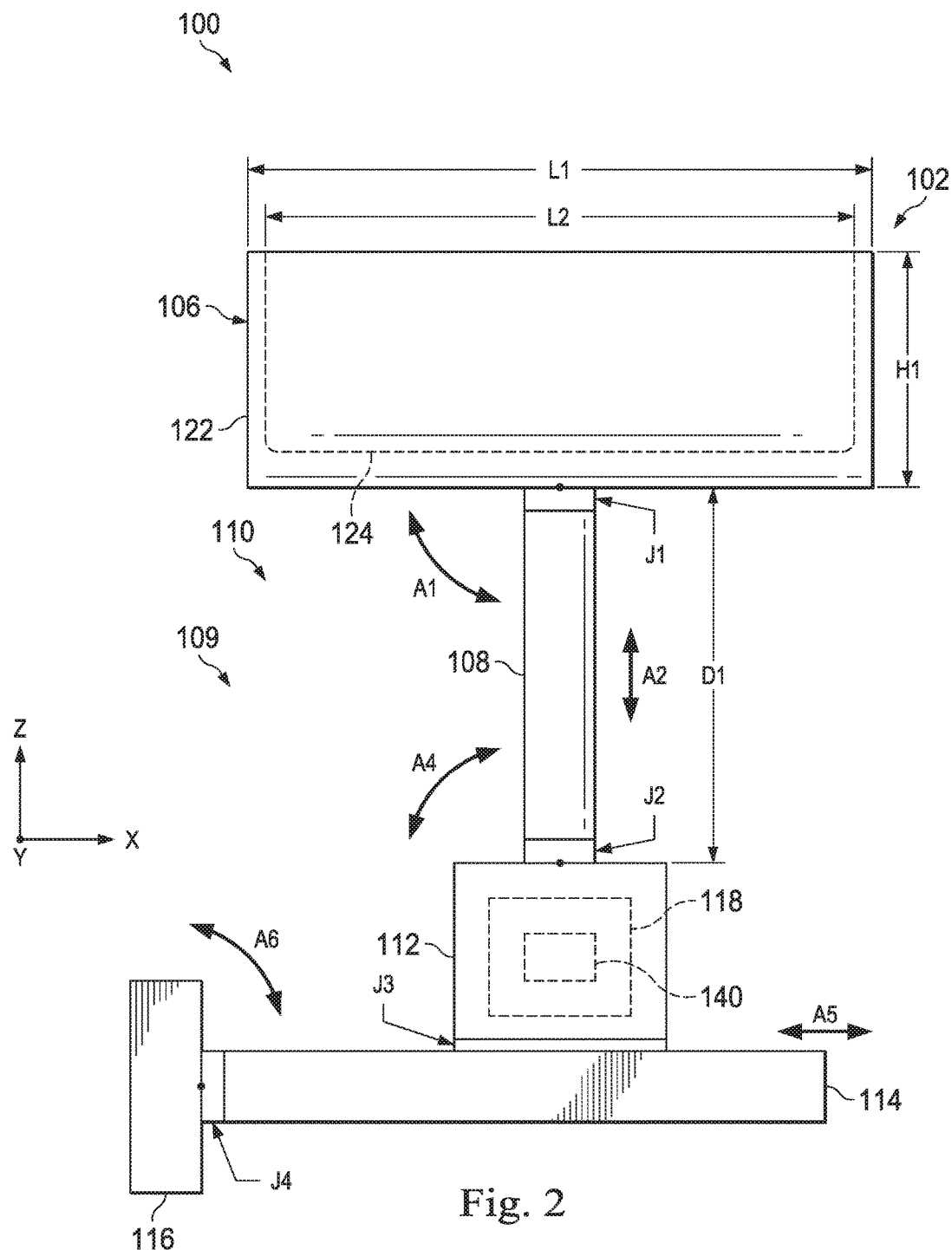
FIG. 2 is an illustration of a side view of the exemplary forearm stabilizing system shown in FIG. 1.

FIG. 2 is an illustration of a side view of the exemplary forearm stabilizing system 100 shown in FIG. 1. The forearm stabilizing system 100 is configured and arranged to support the weight of a surgeon's arms while he or she performs a surgical procedure over a patient.

In this configuration, a surgeon (e.g., an ophthalmologist) may perform surgery on a patient lying supine on the operating table 1 (FIG. 1). In general, a surgeon performs ocular surgery while looking through the eyepieces 14 of the microscope 5 or at a magnified image of the patient's eye. The forearm stabilizing system 100 is designed to reduce inadvertent surgeon motion that occurs as a result of natural breathing, fatigue, or medical conditions (e.g., high velocity motion such as tremor), while facilitating smooth intentional motion (i.e., generally low velocity motion) throughout the surgical procedure to avoid injury to the patient. In some instances, the surgeon rests a portion of his or her hands on the patient's head as he or she performs the surgery in an attempt to coordinate his or her own movement with that of the patient. This technique also may be used with the arm stabilization member 102 positioned close to the patient's head. Furthermore, the arm stabilization member 102 may lend additional stability to the surgeon-patient contact by counteracting the unfavorable motions of the surgeon and providing stable operating conditions.

As shown in FIG. 2, the arm stabilization member 102 may include an arm support 106, here shown as a U-shaped cradle and a movement mechanism 110. The movement mechanism 110 is configured and arranged to support the arm support 106 and to enable it to move or be moved to a desired location relative to the patient and that is comfortable for the surgeon.

Figure 3:
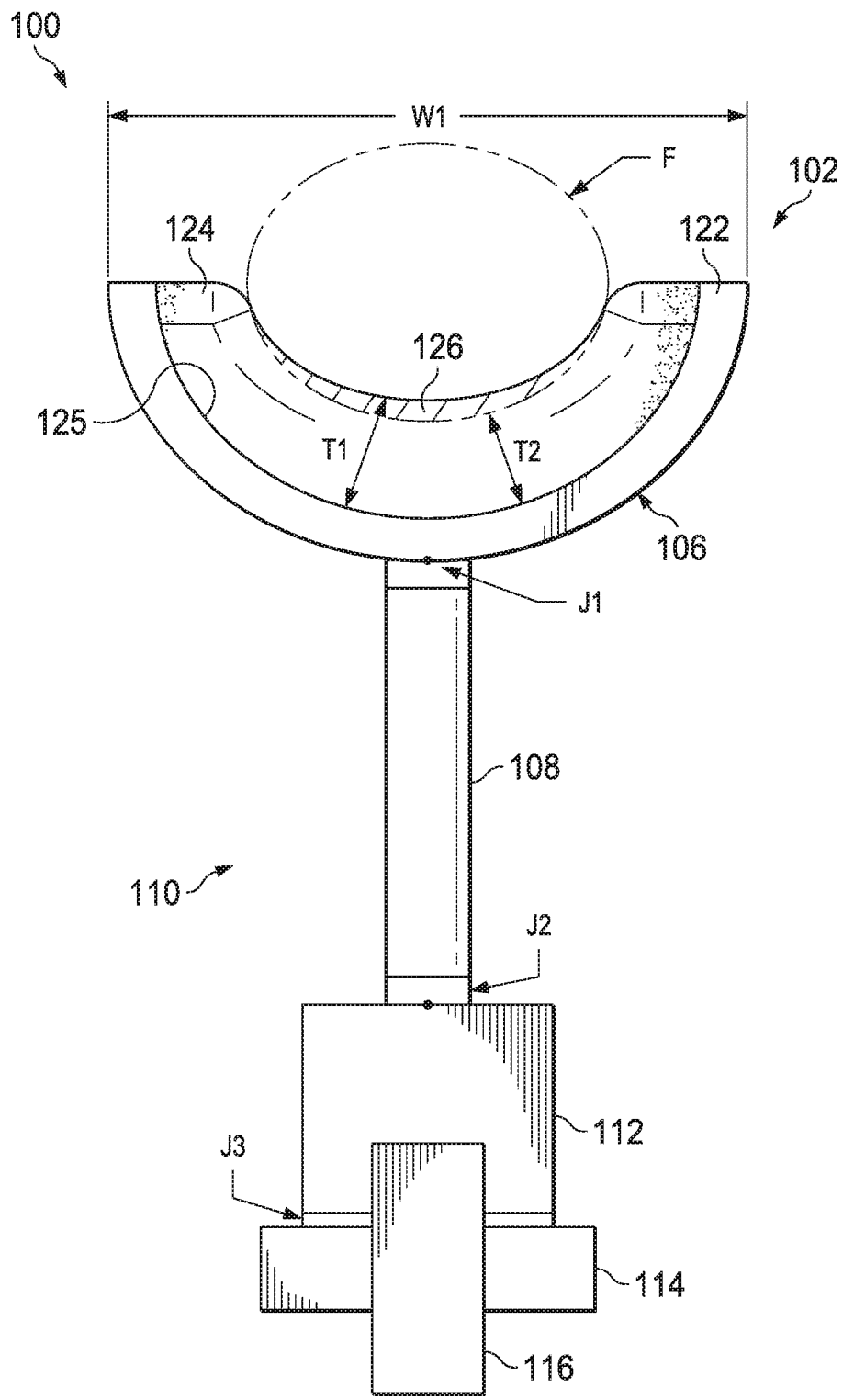
FIG. 3 is an illustration of a front end view of the exemplary forearm stabilizing system shown in FIG. 1.

The arm support 106 will be described first with reference to FIGS. 2 and 3. FIG. 3 is an illustration of a front end view of the exemplary forearm stabilizing system 100 shown in FIG. 1. As shown in FIG. 3, the arm support 106 of the arm stabilization member 102 is configured to partially encircle or cradle the surgeon's forearm F. The arm support 106 comprises an outer frame 122 lined by an inner pad 124. The inner pad 124 is configured and arranged to provide a dampening effect that minimizes inadvertent motion, such as tremors, of the surgeon. In the pictured embodiment, the outer frame 122 and the inner pad 124 of the arm support 106 are shaped as hollowed out, semi-cylindrical structures. In other embodiments, the outer frame 122 and the inner pad 124 may be shaped differently and have different angles of curvature than shown herein. The shape and size of the arm support 106 is selected to provide optimal support and comfort to the arm of the surgeon. In some embodiments, the arm support 106 may be available in different sizes and shapes to accommodate the varying anatomical shapes and sizes of various users.

Referring to both FIGS. 2 and 3, the outer frame 122 is made of a relatively rigid material (e.g., plastic, polymer, metal, stainless steel, and anodized aluminum) that is sufficiently firm to support the weight of a surgeon's forearm for the duration of a surgical procedure. The outer frame 122 is sized to receive and support a portion of the surgeon's forearm and/or wrist. As shown in FIG. 2, the outer frame 122 includes a length L1 ranging from 15 cm (centimeters) to 50 cm. For example, in one embodiment, the length L1 measures 25 cm. In some embodiments, the inner pad 124 has a length L2 that is substantially equivalent to the length L1 of the outer frame 122. In other embodiments, the inner pad 124 has a smaller length L2 than the length L1 of the outer frame 122, as shown in FIG. 2. The outer frame 122 includes a height H1 ranging from 5 cm to 15 cm. For example, in one embodiment, the height H1 measures 7 cm. Returning to FIG. 3, the outer frame 122 includes a width W1 ranging from 10 cm to 25 cm. For example, in one embodiment, the width W1 measures 15 cm. These measurements are provided only as examples, and other measurements and ranges are contemplated.

The inner pad 124 lines at least a portion of an inner surface 125 of the outer frame 122, as shown in FIG. 3. The inner pad 124 comprises a soft pad that is configured to conform to the surgeon's forearm F (as indicated by the cross-hatched area 126, representing compressed pad material) and provide a supportive and comfortable arm rest throughout the duration of the surgery while simultaneously dampening inadvertent movement of the surgeon's forearm. For example, when the surgeon rests his or her forearm F within the arm support 106, a first thickness T1 of the inner pad 124 may decrease to a second thickness T2. The thickness T1 may range from 10 mm (millimeters) to 40 mm. For example, in one embodiment, the thickness T1 is 25 mm. The thickness T2 may range from 5 mm to 35 mm. For example, in one embodiment, the thickness T2 is 20 mm. These measurements are provided only as examples, and other measurements and ranges are contemplated.

In some embodiments, the inner pad 124 is formed at least partially of a high-density, viscoelastic material, such as viscoelastic foam, that may dampen inadvertent movements of the surgeon's forearm F. Viscoelastic foam is an open-celled material that is temperature and weight sensitive, becoming more soft and pliable with increases in temperature. Viscoelastic foam conforms to body shape due to a combination of weight distribution and the increase in temperature associated with body contact. As the position of the heat-producing body part (e.g., the surgeon's forearm) changes, the viscoelastic foam adjusts to the resulting shape. An example of this type of viscoelastic foam is the material used inside a TempurPedic® mattress. In contrast to a lower-density, non-viscoelastic pad (such as, by way of non-limiting example, a springy foam air cell pad), the forearm F can be dynamically supported throughout the surgery as the surgeon shifts his or her forearm F within the arm support 106 because the viscoelastic material compresses to a greater extent in areas around the forearm F where body temperature and weight are the highest, thereby better alleviating the surgeon's arm pain and/or arm fatigue. In some embodiments, the inner pad 124 additionally comprises a layer of polyurethane foam. In some embodiments, it is contemplated that the inner pad 124 includes a cover having pockets or openings beneath the visco-elastic layer to allow for the insertion of pad inserts (e.g., pad inserts having different densities and/or levels of firmness) within the arm support 106 to adjust the firmness according to a surgeon's personal preference.

The movement mechanism 110 may include a linkage 109 formed of a plurality of links connected by joints (identified in FIG. 2 as joints J1, J2, J3, and J4). The movement mechanism 110 may also include controllable actuators, springs, or other components that cooperate to support the arm support 106 and enable it to move. In this exemplary embodiment, the linkage 109 includes links identified herein as an elongate shaft 108, a housing 112, and a base 114. These links (e.g., the elongate shaft 108, the housing 112, and the base 114) may be supported by a connector 116 that may connect the linkage 109 and the arm support 106 to a solid support structure such as the operating table 1. In addition, these links (e.g., the elongate shaft 108, the housing 112, and the base 114) may support the arm support 106.

The plurality of joints J1, J2, J3, and J4 connect links of the linkage 109 to each other, to the connector 116, and to the arm support 106. More specifically, as shown in FIG. 2, the joint J1 may be disposed between the arm support 106 and the shaft 108. The joint J2 may be disposed between the shaft 108 and the housing 112. The joint J3 may be disposed between the housing 112 and the base 114. The joint J4 may be disposed between the base 114 and the connector 116. The joints J1-J4 may be any of a variety of types of kinematic joints, including without limitation, revolving, rotating, and translating joints. In some implementations, any one or more of the joints J1-J4 are universal joints permitting rotation and/or pivoting in more than one plane. In various embodiments, the joints J1-J4 may be manually operable, mechanically operable, electronically operable, or any combination of these.

In the embodiment shown in FIG. 1, the connector 116 anchors the arm stabilization member 102 to the operating table 1. The connector 116 and the base 114 may create a stable platform for the arm support 106. Such a stable platform may help to minimize involuntary surgeon movement. In some embodiments, the connector 116 is adjustable to set the arm stabilization member 102 at a desired height above the operating table 1 in order to optimize surgeon comfort.

In the pictured embodiment, the base 114 is a rectangular platform shaped and sized to support the arm support 106 and the shaft 108. As described below in greater detail with reference to FIG. 5, the shaft 108 and housing 112 may translate linearly on the x-axis by sliding on a track 150 (shown in FIG. 5) that extends on the base 114, thereby bringing the user's arm (resting in the arm support 106) closer to or farther from the operating table 1. The track 150 is also represented herein as the translational joint J3. In particular, the user may shift the shaft 108, housing 112, and arm support 106 on the track 150 in the directions indicated by the arrows A5 to a desired position.

The shaft 108 is shaped and sized to support the arm support 106, and may contain various components of the movement mechanism 110, including parts of a counterbalance system 118 (shown as a box in the housing 112), which functions to provide an appropriate counterbalancing force to the forces exerted by surgeon's arm and gravity upon the arm stabilization member 102, and in particular upon the arm support 106. In some embodiments, the shaft 108 comprises multiple links that may articulate or bend relative to one another. In other instances, the shaft 108 is a monolithic, linear component.

In the pictured embodiment, the shaft 108 couples to the housing 112, and the housing 112 couples to the base 114. The housing 112 is shaped and sized to contain various components of the movement mechanism 110, and may include components of the counterbalance system 118. Other embodiments may lack a housing 112, and the shaft 108 may be coupled directly to the base 114.

In the embodiments described herein, the movement mechanism 110 comprises a serial kinematic mechanism including the joints J1, J2, J3, and J4 disposed between and connecting the arm support 106, the shaft 108, the housing 112, the base 114, and/or the connector 116. More specifically, the movement mechanism 110 includes rigid links of the linkage 109 (e.g., the shaft 108, the housing 112, the base 114, and/or the connector 116) coupled together by rotational, revolving, and/or translational joints (e.g., the joints J1-J4). In some implementations, any element of the linkage 109 (e.g., the shaft 108, the housing 112, the base 114, and/or the connector 116) to be in the form of a 4-bar linkage, referred to herein as a parallelogram arrangement. This type of parallelogram arrangement for any link of the linkage 109 may enable the arm support 106 to maintain a particular tilt or angle, even as its elevation or side to side position changes. In some implementations, the joint J1 is arranged to allow the arm support 106 to pivot or rotationally displace about the joint J1 in the direction indicated by the arrow A1 in FIG. 2 (i.e., pitch motion). In addition, the joint J1 may be arranged in order to permit rotation of the arm support 106 in the direction indicated by the arrows A3 in FIG. 5 (i.e., yaw motion). In some embodiments, the joint J2 may enable the shaft 108 to pivot about the joint J2 in the directions indicated by the arrows A4 in FIG. 2. Thus, while resting within the arm support 106, the surgeon's forearm is able to move in the pitch (i.e., rotation about the side-to-side axis at the joint J1) and yaw (i.e., rotation about the vertical axis at the joints J1 and/or J2) axes of rotation. In some embodiments, the joint J3 may enable the elongate shaft 108 and the housing 112 to shift, translate, or laterally displace along the x-axis on the base 114 in the directions indicated by the arrows A5 in FIG. 2. In some embodiments, the joint J4 may enable the base 114 to pivot in the directions indicated by the arrows A6 in FIG. 2. Additional movements between the links or components of the movement mechanism 110 of the arm stabilizing system 100 are discussed below with reference to FIG. 5. In some embodiments, dashpots (e.g., rotary and/or linear dashpots) or other suitable damper components may be positioned at the joints J1-J4 to act as shock absorbers that provide additional dampening as the arm support 106 moves relative to the operating table 1.

Figure 4:
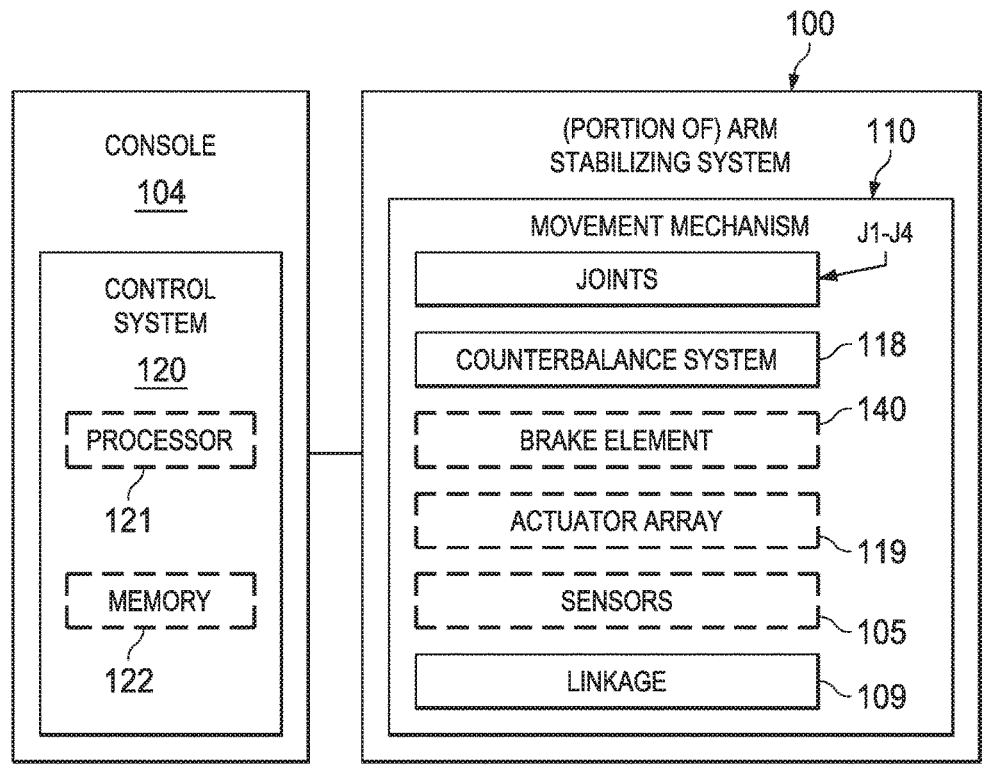
FIG. 4 is a block diagram of an exemplary embodiment of a portion of an exemplary arm stabilizing system according to an aspect of the present disclosure.

FIG. 4 is a block diagram of an exemplary embodiment of a portion of the arm stabilizing system 100 according to an aspect of the present disclosure. Optional components, including components that may form part of an exemplary powered system, are outlined in dashed lines. As shown in FIG. 4, the movement mechanism 110 includes the counterbalance system 118 which, as described above, functions to provide an appropriate counterbalancing force to the forces exerted by surgeon's arm and gravity upon the arm stabilization member 102, and in particular upon the arm support 106. The counterbalance system 118 may cooperate with the linkage 109 and the joints J1-J4 in a manner that counters the forces exerted by the weight of the surgeon's arm on the arm support 106. In some embodiments, the counterbalance system 118 functions as a gravity compensation feature which may render the mechanical load of the surgeon's arm effectively weightless or low weight for easy arm positioning. It may do this in any of a variety of ways. For example, in some implementations, the counterbalance system 118 may include a series of springs, and one or more links of the linkage 109 may be a 4-bar linkage. In one such implementation, the shaft 108 may be formed of a 4-bar linkage and the counterbalance system 118 may comprise springs such as coil springs extending from one bar to the other in a manner that offsets or compensates for loading applied on the shaft 108. In another embodiment, the shaft 108 may be formed of a 4-bar linkage and the counterbalance system 118 may comprise gas springs extending from one bar to the other in a manner that offsets or compensates for loading applied on the shaft 108. In other implementations, the counterbalance system 118 may comprise one or more motors disposed at any of the joints J1-J4 to control pivoting, rotation, translation, or other movement at any one or more the joints. In some implementations, the motors control motor torque as a function of mechanical load position. In yet other implementations, the counterbalance system 118 comprises gas springs that may balance mechanical load. Yet other implementations use other systems that may balance the mechanical load. The counterbalance system 118 may be selected (e.g., by choice of spring strength, mounting points, range spring of motion, motor torque, and the like) to provide near-neutral weight balance to the arm support 106 through its range of operative motion.

In one example, the counterbalance system 118 operates with at least one parallelogram-link structure, which may be, for example any link of the linkages 109, and which is force balanced in the vertical plane indicated by the z-axis by one or more counterbalance elements (e.g., gas-springs). In this implementation, balancing in the vertical plane along the z-axis may be provided by a conventional gas spring of selected dimensions, spring characteristics, and mounting points, so as to provide light positioning action, and desirable force and inertia matching in X, Y, and Z directions. The balance characteristics may be selected to be near-neutral throughout the range of motion, or may be bi-stable, so as to have predetermined raised and lowered stability points. Optionally, the parallelogram-link structures may be balanced by counterweights, tension springs, torsion springs, compression springs, air or hydraulic cylinders, torque motors, or combinations of these devices. Each parallelogram-link may be raised and lowered vertically along the z-axis with minimal residual force (e.g., from the surgeon's forearm) because the counterbalance features (e.g., the gas springs) are configured to support the majority of the system weight throughout the range of motion. Such a parallelogram-link may be mounted to a joint (e.g., the joint J1 shown in FIG. 1) to provide rotation in the horizontal plane as indicated by the x-y axis (indicated by the arrows A3 in FIG. 5).

The movement mechanism 110 of the arm stabilization member 102 may comprise a passive or an active mechanism that creates movement or displacement of the arm support 106. Although the arm support 106 is typically manually positioned, one or more joints J1-J4 of the movement mechanism 110 may be power operated and may be computer controlled by the control system 120. For example, one or more of the links (e.g., the shaft 108, the housing 112, and/or the base 114) and/or joints J1-J4 of the movement mechanism 110 may be powered via actuators that assist motion of the arm support 106 in the x, y, and z axes and/or the counterbalancing function. As indicated by the dashed boxes in FIG. 4, in some active embodiments, the movement mechanism 110 of the arm stabilization member 102 includes an actuator array 119 and is in communication with a control system 120. The control system 120 may be housed in the control console 104 as shown or elsewhere within the surgical environment. In some embodiments, the control system 120 may recognize the position of the arm support 106 relative to the surgical environment (e.g., relative to the patient and/or the operating table 1) and signal the actuator array 119 (e.g., via command signals) to change the position of the arm support 106 by moving it to a desired position, such as, for example, a default position. FIG. 1 shows the arm stabilization member 102 connected to the console 104 by means of the communication cable 103. The communication cable 103 may be an electrical cable that carries signals and communications between the control system 120 in the control console 104 and the arm stabilization member 102. However, it should be apparent that in some embodiments, wireless communication between the console 104 and the arm stabilization member 102 may be used.

The control system 120 may include a processor 121 and/or a memory 122. In some implementations, the processor 121 may be an integrated circuit with power, input, and output pins capable of performing logic functions. In some implementations, the processor 121 is a controller that controls different components that perform different functions. In some embodiments, this control system 120 may analyze sensor data and send signals to the actuator array 119 of the arm stabilization member 102 to actively and dynamically regulate movement speed to provide a smooth motion to the arm support 106 and/or reduce motion of the surgeon's arm. In one implementation, this may be accomplished by applying dynamic forces to resist motion. In some embodiments, the control system 120 uses an algorithm employing logic control or an alternative learning based control to produce these signals. In some instances, the memory 122 may store the individual preferences of a particular surgeon (e.g., the angular position of the arm support 106 relative to the operating table 1). The memory 122 may be a semiconductor memory that interfaces with the processor. In one example, the processor 121 can write to and read from the memory 122. For example, the processor 121 can be configured to read data from the sensor system and write that data to the memory 122. In this manner, the control system 120 can generate signals based on data or executable programs stored in the memory to control the forearm stabilizing system 100. The control system 120 may also perform other basic functions, such as erasing or overwriting the memory 122, detecting when the memory 122 is full, and other common functions associated with managing semiconductor memory.

The actuator array 119 may be made up of a plurality of individual actuators that, in some embodiments, are actuatable independent of one another to affect the links and linkages of the movement mechanism 110. The actuators of the actuator array 119 may be coupled to the joints J1-J4 within the forearm stabilizing system 100 in a manner that allows them to affect the movement of the links. In some embodiments, the actuator array 119 may be formed of a series of electrically driven actuators. In one implementation, the actuator array 119 comprises a series of motors arranged and programmed to provide torque resistance that compensates for loading at the joints J1-J4. In such implementations, one or more motors may be associated with each of the joints J1-J4. The motor may be actuated to provide torque resistance to stabilize its adjacent links, or may be actuated to provide movement at the joint or accomplish a desired displacement of the adjacent links. In one embodiment, the actuators are electromechanical linear actuators operable under the control of the control system 120. In another embodiment, the actuators are pneumatic or hydraulic actuators that facilitate precise position control under the control of the control system 120. The actuators of the actuator array 119 are configured and arranged to engage the joints J1-J4 and, under the control of the control system 120, reposition or adjust the position of the arm support 106 relative to the patient during the surgical procedure to best accommodate the surgeon's operating angle.

In some embodiments, the movement mechanism 110 includes sensors 105 that may be motion, shape, and/or position sensors arranged and configured to detect the position of the arm support 106 relative to the patient and/or the operating room (e.g., the operating table 1 and/or the surgical microscope 5). These sensors 105 may include, for example, vibrating structure gyroscopes (e.g. MEMS (Micro-Electro-Mechanical Systems) three-axis gyroscopes), accelerometers, or other types of motion detecting sensors. Alternatively, the sensors 105 may include a machine vision target and one or more imaging devices such as cameras or lasers. The position of the target may then be recorded by the cameras or tracked by the lasers to provide precise motion data.

The control system 120 may use the data sensed by the sensors 105 to determine the appropriate positional adjustments of the arm support 106. In some embodiments, the control system 120 is in communication with the sensors 105 and individual actuators of the actuator array 119. The control system 120 may be programmed or arranged to control the actuator array 119 based on feedback or other information from the sensors 105. After analyzing the sensed data inputs, the control system 120 sends control signals to the actuator array 119 to counterbalance loads applied on the arm stabilizing system. In some implementations, the control system 120 may process data from the sensors 105 to determine velocity or acceleration of arm movements and may actively counter high velocity or high acceleration motion, which may be indicative of, for example, a tremor, and may not counter low velocity or low acceleration motion that may be indicative, for example, intentional motion. In some embodiments, acceleration thresholds for determining the amount of counter motion may be determined through user input (e.g., graphical user input, switches, etc. to indicate a level of sensitivity). Other sensitivity determinations are also contemplated.

The structures of the movement mechanism 110 (e.g., including the linkage 109, the counterbalance system 118, and/or any of the joints J1-J4) may be lockable to prevent inadvertent movement once the arm support 106 is in the selected alignment and position relative to the patient. As shown in FIGS. 2 and 4, some implementations of the movement mechanism 110 include a brake element 140 configured to immobilize or arrest motion of one or more of the joints J1, J2, J3, and/or J4 to hold the arm support 106 in position within the surgical environment. As described above, the arm support 106 may be repositioned freely in pitch and yaw directions as well as along the x, y, and z axes. After the arm support 106 has been optimally positioned for the individual user, the arm support 106 may be locked in position using the brake element 140. The arm support 106 may be immobilized until the brake element 140 is released, at which time the surgeon moves the arm support 106 to another desired position. The user may then reapply the brake element 140 to hold the arm support 106 at the new position. In some implementations, the brake element 140 is a power-driven brake element, including one or more electric, pneumatic, or hydraulic actuator or motor, that operates to immobilize the arm support 106. In some implementations, the brake element 140 is one or more torque motors as described herein, controlled to immobilize the arm support 106. In some implementations, a user may activate or deactivate the brake element 140 using an input on the console 104. For example, the input may be a knob, a button, a switch, or other input device that may be activated by a user. In other implementations, the brake element 140 is a mechanical feature that may cooperate with and immobilize the joints J1-J4. A user may activate or deactivate mechanical brake elements using, for example and without limitation, a manually operated cam that may create braking friction between components at the joints. Other types of break elements are also contemplated. In some implementations, a user may activate a brake element 140 on any single or plurality of joints without activating a brake element 140 on different joints.

In some embodiments, the brake element 140 operates as a continuous lock of one or more of the joints J1-J4 of the movement mechanism 110 that may be inactivated by intentional movements of the user (e.g., low velocity and/or high force motion), thereby allowing the links to move relative to each other. For example, in some embodiments, the brake element 140 may be configured to continuously arrest motion of the joints L1-L4 of the movement mechanism 110 until the user applies sufficient lateral force (e.g., the dynamic load of the surgeon's arm moving laterally) on the arm support 106, upon which the brake element 140 is inactivated and the joints are unlocked and free to move. In some elements, the brake element 140 includes torque motors that generally arrest motion of the joints J1-J4, but allow motion of the joints J1-J4 in response to a consistent lateral load past a predefined amount.

Figure 5:
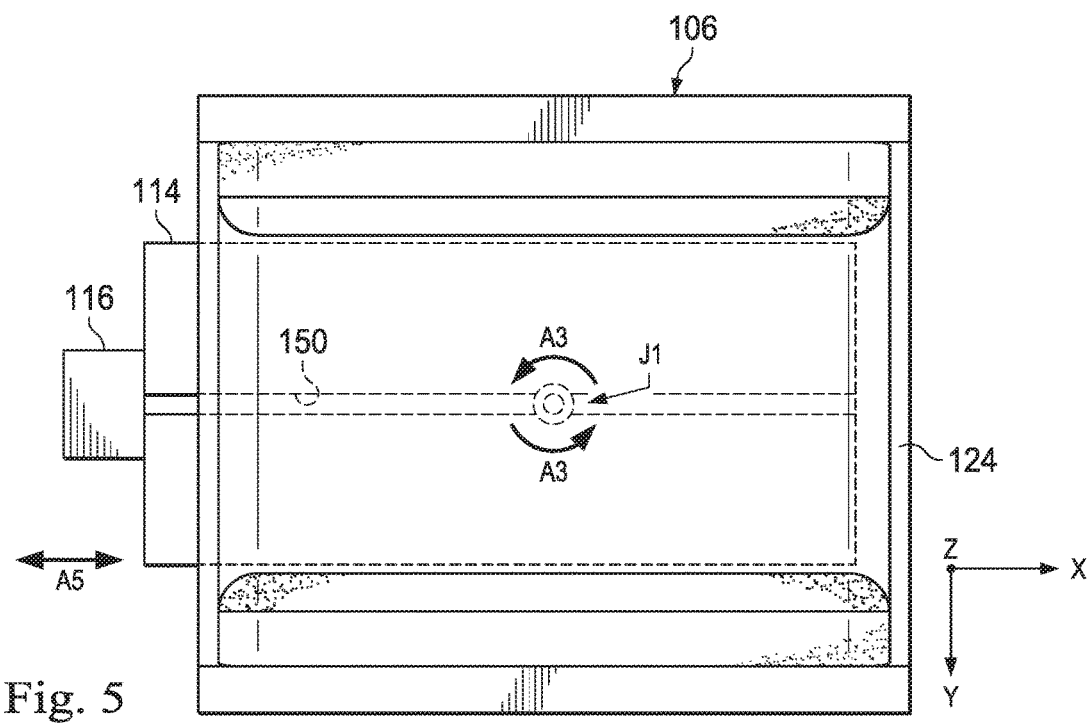
FIG. 5 is an illustration of a top view of the exemplary forearm stabilizing system shown in FIG. 1.

FIG. 5 is an illustration of a top view of the exemplary forearm stabilizing system shown in FIG. 1. As mentioned above in relation to FIG. 2, the arm support 106 may pivot about the joint J1 in the directions indicated by the arrows A1 in FIG. 2 and by the arrows A3 in FIG. 5. Moreover, as the surgeon rests the weight of his or her arm upon the inner pad 124, the joint J1 may shift vertically in space in the directions of the arrows A2 along the z-axis indicated in FIG. 2. In other words, a distance D1 between the arm support 106 and the housing 112 may change in reaction to the weight of the surgeon's arm and/or the force and directionality of his or her movements. In this sense, the distance D1 is a dynamic length. The counterbalance system 118 acts to smooth this transition and lend a sensation of weightlessness or weightless support to the surgeon. Returning to FIG. 5, the arm support 106 may rotate about the vertical z-axis around the joint J1 (e.g., rotation in the yaw direction about a rotational joint that permits movement in the pitch and yaw directions while preventing movement in the roll directions). In FIG. 5, the vertical z-axis extends perpendicular to the page of the illustration.

In addition, the arm support 106 and the shaft 108 (not visible in FIG. 5 and best seen in FIG. 2) may translate linearly on the x-axis by sliding on a track 150 extending on the base 114. In some instances, the user may shift the shaft 108 and arm support 106 on the track 150 in the directions indicated by the arrows A5 to a desired position and apply one of the brake elements 140 to lock the position of the shaft 108 relative to the operating table 1 before beginning the surgical procedure. In some embodiments, this motion is manually controlled. In some embodiments, this motion may additionally or alternatively be powered and controllable by the control system 120.

Accordingly, the arm stabilizing systems described herein may improve the surgical experience by more comfortably supporting the surgeon's operating arm than conventional rigid supports, and by dampening inadvertent motion by cradling the arm upon a viscoelastic pad while permitting intentional repositioning (e.g., in the pitch, yaw, horizontal, and/or vertical directions) and locking of the arm support throughout the surgical procedure. Moreover, the movement mechanism and counterbalance systems described herein provide a "weightless" sense of support to the surgeon, which may decrease surgeon fatigue and discomfort during the surgical procedure. The reduced motion and "weightless" support can result in better physician control of instruments and tools while minimizing surgeon discomfort and fatigue, thereby contributing to an improved surgical outcome for the patient.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. An arm stabilizing system for dampening inadvertent movement of an arm of a user during a surgical procedure, comprising:
    an arm stabilization member arranged to support the arm of the user, the arm stabilization member comprising:
        an arm support comprising an outer frame sized to support at least a portion of the user's arm and an inner pad lining an inner surface of the outer frame, the inner pad configured to conform to the user's arm, and
        a movement mechanism coupled to the arm support, the movement mechanism comprising a plurality of links movably connected by joints, the movement mechanism configured to compensate for gravitational forces exerted by the arm of the user, wherein each joint is regulated by one or more motors and wherein the joints are universal joints to permit rotation and pivoting in more than one plane; and
    a brake element configured to arrest movement between two or more of the plurality of links of the movement mechanism.

2. The arm stabilizing system of claim 1, wherein the arm stabilization member is affixed to an operating table.

3. The arm stabilizing system of claim 2, wherein the plurality of links of the movement mechanism include an elongate shaft and a base coupled to the elongate shaft, wherein the elongate shaft is repositionable along a longitudinal axis of the base.

4. The arm stabilizing system of claim 1, wherein the inner pad is formed of a viscoelastic material.

5. The arm stabilizing system of claim 4, wherein the viscoelastic material comprises a viscoelastic foam.

6. The arm stabilizing system of claim 1, further comprising a cover disposed around the inner pad, the cover including pockets configured to receive pad inserts.

7. The arm stabilizing system of claim 1, wherein the movement mechanism is configured to provide near-neutral weight balance to the arm support through a range of operative motion of the arm support.

8. The arm stabilizing system of claim 1, wherein the movement mechanism is configured to provide bi-stable weight balance to the arm support.

9. The arm stabilizing system of claim 1, wherein the movement mechanism is powered.

10. The arm stabilizing system of claim 9, further comprising a control system coupled to the movement mechanism, wherein the joints of the movement mechanism are mechanically responsive to command signals from the control system.

11. The arm stabilizing system of claim 1, further comprising a control system coupled to the movement mechanism, wherein the joints of the movement mechanism are mechanically responsive to command signals from the control system.

12. An arm stabilization member for dampening inadvertent movement of an arm of a user during a surgical procedure, comprising:
 an arm support comprising an outer frame sized to support at least a portion of the user's arm and an inner pad lining an inner surface of the outer frame, the inner pad configured to conform to the user's arm; and
 a movement mechanism coupled to the arm support, the movement mechanism comprising a plurality of links movably connected by joints, the movement mechanism configured to compensate for gravitational forces exerted by the arm of the user, wherein each joint is regulated by one or more motors and wherein the joints are universal joints to permit rotation and pivoting in more than one plane.

13. The arm stabilization member of claim 12, further comprising a connector, the connector configured to removably couple the arm stabilization member to an operating table.

14. The arm stabilization member system of claim 12, wherein the plurality of links include an elongate shaft and a base coupled to the elongate shaft, wherein the elongate shaft is repositionable along a longitudinal axis of the base.

15. The arm stabilization member system of claim 12, wherein the inner pad is formed of a viscoelastic material.

16. The arm stabilization member system of claim 12, wherein the movement mechanism is configured to provide near-neutral weight balance to the arm support through a range of operative motion of the arm support.

* * * * *